(12) United States Patent
Eskuri

(10) Patent No.: US 6,752,825 B2
(45) Date of Patent: Jun. 22, 2004

(54) NESTED STENT APPARATUS

(75) Inventor: Alan Eskuri, Hanover, MN (US)

(73) Assignee: SciMed Life Systems, INC, Maple Grove, MN (US)

( * ) Notice: Subject to any disclaimer, the term of this patent is extended or adjusted under 35 U.S.C. 154(b) by 10 days.

(21) Appl. No.: 09/969,967

(22) Filed: Oct. 2, 2001

(65) Prior Publication Data

US 2003/0065375 A1 Apr. 3, 2003

(51) Int. Cl.$^7$ .................................................. A61F 2/06
(52) U.S. Cl. ...................................................... 623/1.12
(58) Field of Search ........................... 623/1.11, 1.12, 623/1.13, 1.23, 1.44, 1.45; 606/108, 159, 191, 192, 194, 195, 198, 200; 604/508–510

(56) References Cited

U.S. PATENT DOCUMENTS

| | | | | |
|---|---|---|---|---|
| 4,744,366 A | * | 5/1988 | Jang | 606/194 |
| 4,994,071 A | | 2/1991 | MacGregor | 606/194 |
| 5,160,342 A | * | 11/1992 | Reger et al. | 606/200 |
| 5,669,924 A | | 9/1997 | Shaknovich | 606/108 |
| 5,718,724 A | | 2/1998 | Goicoechea et al. | 623/1 |
| 5,720,735 A | | 2/1998 | Dorros | 604/284 |
| 5,723,004 A | | 3/1998 | Dereume et al. | 623/1 |
| 5,749,825 A | | 5/1998 | Fischell | 600/3 |
| 5,755,735 A | | 5/1998 | Richter et al. | 606/194 |
| 5,807,398 A | * | 9/1998 | Shaknovich | 623/1.11 |
| 5,820,595 A | * | 10/1998 | Parodi | 604/101.05 |
| 5,824,054 A | * | 10/1998 | Khosravi et al. | 623/1.44 |
| 5,833,694 A | | 11/1998 | Poncet | 606/108 |
| RE35,988 E | * | 12/1998 | Winston et al. | 623/1 |
| 5,976,181 A | * | 11/1999 | Whelan et al. | 623/1.12 |
| 6,027,519 A | | 2/2000 | Stanford | 606/198 |
| 6,051,020 A | | 4/2000 | Goicoechea et al. | 623/1 |
| 6,096,073 A | | 8/2000 | Webster et al. | 612/1.16 |
| 6,123,723 A | * | 9/2000 | Konya et al. | 623/1.11 |
| 6,129,738 A | | 10/2000 | Lashinski et al. | 606/194 |
| 6,224,609 B1 | | 5/2001 | Ressemann et al. | 606/108 |
| 6,253,769 B1 | | 7/2001 | LaFontaine et al. | 128/898 |
| 6,254,628 B1 | * | 7/2001 | Wallace et al. | 623/1.12 |
| 6,258,117 B1 | | 7/2001 | Camrud et al. | 623/1.16 |
| 6,325,823 B1 | * | 12/2001 | Horzewski et al. | 623/1.16 |
| 6,443,971 B1 | * | 9/2002 | Boylan et al. | 606/200 |

\* cited by examiner

*Primary Examiner*—Kevin T. Truong
(74) *Attorney, Agent, or Firm*—Vidas, Arrett & Steinkraus P.A.

(57) ABSTRACT

A stent delivery catheter comprises an inner member having a first stent disposed thereabout and a second stent disposed about the first stent. The catheter further comprises a first retractable sheath between the first stent and the second stent, and a second retractable sheath disposed about the second stent.

16 Claims, 6 Drawing Sheets

NESTED STENT APPARATUS

CROSS-REFERENCE TO RELATED APPLICATIONS

Not Applicable

STATEMENT REGARDING FEDERALLY SPONSORED RESEARCH

Not Applicable

BACKGROUND OF THE INVENTION

This invention relates to implantable medical devices and delivery systems for delivering such medical devices into a body lumen.

Percutaneous transluminal coronary angioplasty (PTCA) is a procedure which is well established for the treatment of blockages in the coronary arteries. Blockages may occur from cholesterol precipitation on the coronary wall which may be in any stage from initial deposit through aged lesions. Coronary arteries may also become blocked due to formation of thrombus.

The most widely used form of percutaneous coronary angioplasty makes use of a dilatation balloon catheter which is introduced into and advanced through a lumen or body vessel until the distal end thereof is at a desired location in the vasculature. Once in position across a lesion site, the expandable portion of the catheter, or balloon, is inflated to a predetermined size with a fluid at relatively high pressures, to radially compress the atherosclerotic plaque of the lesion against the inside of the artery wall and thereby dilate the lumen of the artery. The balloon is then deflated to a small profile so that the dilatation catheter may be withdrawn from the patients vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To reduce restenosis and strengthen the area, a physician can implant an intravascular prosthesis for maintaining vascular patency, such as a stent, inside the artery at the lesion.

Expandable, implantable medical devices such as stents are utilized in a number of medical procedures and situations as are stent delivery assemblies. As such, their structure and function are well known. A stent is a generally cylindrical prosthesis introduced via a catheter into a lumen of a body vessel in a configuration having a generally reduced diameter and then expanded to the diameter of the vessel. The stent may be self-expanding, such as a nitinol shape memory stent, or it may be expandable by means of an inflatable portion of the catheter, such as a balloon. In its expanded configuration, the stent supports and reinforces the vessel walls while maintaining the vessel in an open, unobstructed condition.

Some stents have been developed specifically to address the problems that arise in the treatment of stenoses at or near the site of a bifurcation of a body lumen are known in the art. Further, single bifurcated stents and grafts have been developed in order to treat such conditions at the site of a branch of a body lumen. A bifurcated stent and/or graft typically comprises a tubular body or trunk and two tubular legs. Examples of bifurcated stents are shown in U.S. Pat. No. 5,723,004 to Dereume et al., U.S. Pat. No. 4,994,071 to MacGregor, and U.S. Pat. No. 5,755,735 to Richter, et al.

Various techniques have been used to deliver multiple prostheses in order to provide radial support to both a main blood vessel, and contemporaneously to side branches of the blood vessel. Examples of catheters for use in treating bifurcated lumens or delivery systems for bifurcated stents, are shown in U.S. Pat. No. 5,720,735 to Dorros, U.S. Pat. No. 5,669,924 to Shaknovich, U.S. Pat. No. 5,749,825 to Fischell, et al., U.S. Pat. No. 5,718,724 to Goicoechea et al., and U.S. Pat. No. 6,129,738 to Lashinski et al. As maybe seen from these references, in most bifurcated stent delivery systems, the bifurcated stent is mounted on a catheter assembly which comprises essentially two balloon catheters mounted in a guide catheter assembly.

Bifurcated stents such as described above are often more bulky than a cylindrical stent having no branches. The delivery systems for use with bifurcated stents are likewise often more bulky than many of those systems for use in delivering branchless cylindrical stents. The delivery systems for such branchless cylindrical stents may also be somewhat less complex than those utilized with bifurcated stents.

A single branchless cylindrical stent however, may be unsuited for treatment of bifurcation. It would be preferable to utilize multiple cylindrical stents that could be placed in and around a bifurcation site to effectively form a stent assembly which functions similarly to a single bifurcated stent. While use of such multiple stent assemblies would avoid the problems associated with bifurcated stents and delivery systems, delivery of multiple stents to a site within the body could be a difficult undertaking requiring several catheters to be sequentially advanced through a vessel or vessels, in order to place each stent at or around the bifurcation. Moreover, by advancing multiple catheters through the body the risk of damaging the vessel(s) through which each of the delivery catheters is advanced is inherently increased.

In light of the above it would be desirable to provide a multiple stent catheter assembly for treatment of a bifurcation or other region of a vessel, which could be readily inserted into the vessel with a single catheter application.

All U.S. patents, applications and all other published documents mentioned anywhere in this application are incorporated herein by reference in their entirety.

BRIEF SUMMARY OF THE INVENTION

This invention relates to a unique stent assembly and delivery system. A stent assembly comprises at least two stents for delivery into one or more predetermined locations in a body lumen, such as a bifurcation of a vessel and surrounding area. In delivering the stent assembly, the stent assembly may be disposed about a portion of a delivery catheter in an at least partially overlapping configuration. Between each stent may be positioned one or more retractable sheaths or sleeves. The outer most stent may also have a retractable sleeve disposed thereabout. The unique configuration of stents and retractable sleeves provides for the ability to utilize a single catheter to deliver multiple stents to one or more locations in a body lumen.

In some embodiments of the invention, a stent delivery catheter is provided for which comprises an inner member having a first stent disposed thereabout and a second stent disposed about the first stent. The catheter further comprises a first sheath between the first stent and the second stent and may have a second sheath disposed about the second stent. The catheter may be configured to deliver stents of any type including self-expandable and balloon expandable stents.

The catheter may be further configured to deliver more than two stents and sheaths. The catheter may be used to deliver stents of different types as well as different sizes.

In some other embodiment of the invention a method of treating a body is provided for which comprises the steps of providing a catheter comprising a plurality of stents including a first stent and a second stent, the first stent extending within the second stent; inserting the catheter in a bodily vessel and delivering the stents to a first desired location within the body; deploying one of the first and second stents at the first desired location; delivering the other of the first and second stents to a second desired location within the body, the second desired location different than the first desired location; deploying the other of the first and second stents at the second desired location.

Further aspects of the invention will become apparent from the detailed description which follows.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
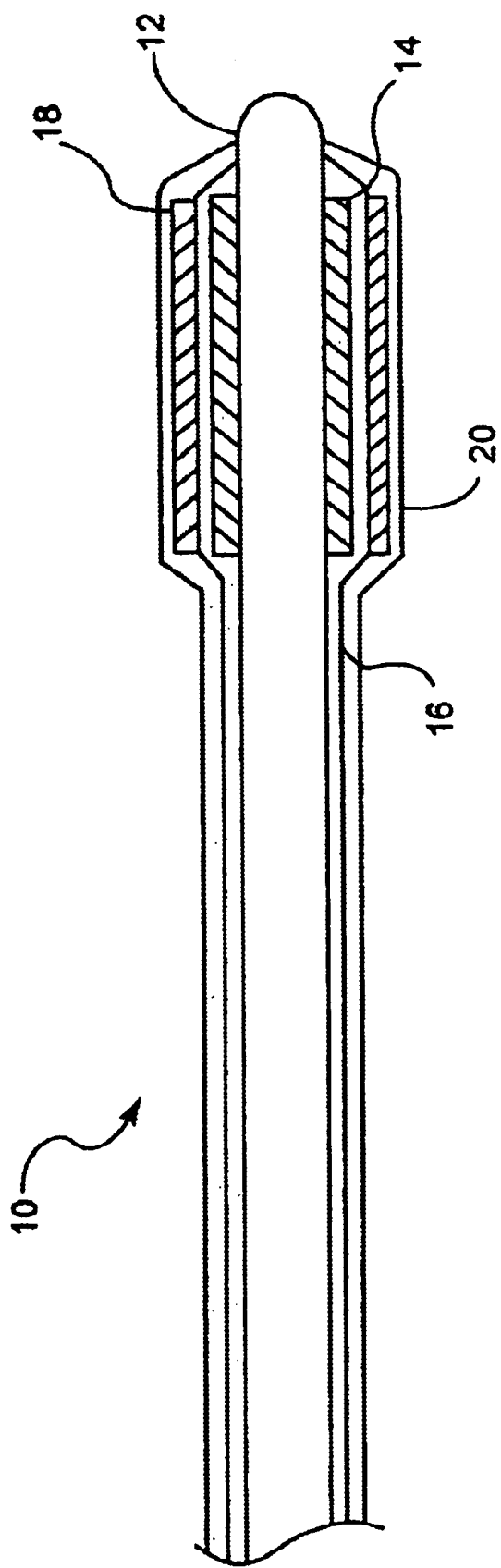
FIG. 1 is a side elevational view of an embodiment of the invention.

While this invention may be embodied in many different forms, there are described in detail herein specific preferred embodiments of the invention. This description is an exemplification of the principles of the invention and is not intended to limit the invention to the particular embodiments illustrated.

The inventive catheters are intended for use in delivering deployable medical devices to a desired location in the body. Desirably, the medical devices are of the radially expandable tubular type. Particularly suitable radially expandable tubular medical devices for use with the inventive catheter include stents, stent-grafts, grafts, vena cava filters and other intraluminal and interluminal prostheses. The devices may be self-expanding or mechanically expandable via balloons or other expansion devices. For the sake of brevity, the term 'stent' as used henceforth, shall be understood to refer to all such radially expandable tubular medical devices.

The inventive medical device delivery catheter in general and stent delivery catheter in particular, may be used for performing one or more intraluminal procedures on a patient as part of a therapeutic treatment. By "intraluminal," it is meant that the procedures occur at a target site within a body lumen. Typically, the procedure will occur within a portion of the patient vasculature such as, for example, the arterial system. More particularly, the inventive catheter will find use in the coronary arteries, the peripheral arteries and the cerebral arteries. The catheters of the present invention, however, are not limited to use in the vascular system and may also be advantageously employed in other body structures, including the prostate via the prostatic urethra, (e.g., to treat benign prostatic hypertrophy (BPH), or adenocarcinoma), the fallopian tube via its lumen (to treat strictures), brain parenchyma (to treat Parkinson's disease), and the like.

The present invention provides for several embodiments of a multiple stent assembly and delivery system. As may be seen in FIG. 1, the delivery system may comprise a catheter assembly, indicated generally at 10. Catheter 10, includes a distal region 12 which as a plurality of stents disposed thereabout. In the embodiment shown in FIG. 1 an inner or first stent 14 is disposed about the distal region 12. The first stent 14 is held in place prior to delivery by a first retractable sheath or sleeve 16 which at least partially overlies first stent 14 at the distal region 12. Disposed about the first stent 14 and first sheath 16 is a second stent 18 which is held in place prior to delivery by a second retractable sheath 20.

Retractable sheaths 16 and 20 extend proximally to the proximal region of the catheter 10 where each of the sheathes 16 and 20 may be proximally retracted. In order to deliver the stents 14 and 18, the outer most sheath 20 must first be retracted to expose stent 18. Stent 18 may then be expanded to a delivery diameter. Once the outermost sheath has been retracted and the immediately underlying stent is expanded, the next innermost sheath, such as sheath 16 may be retracted and the underlying stent 14 may be expanded.

Figure 2:
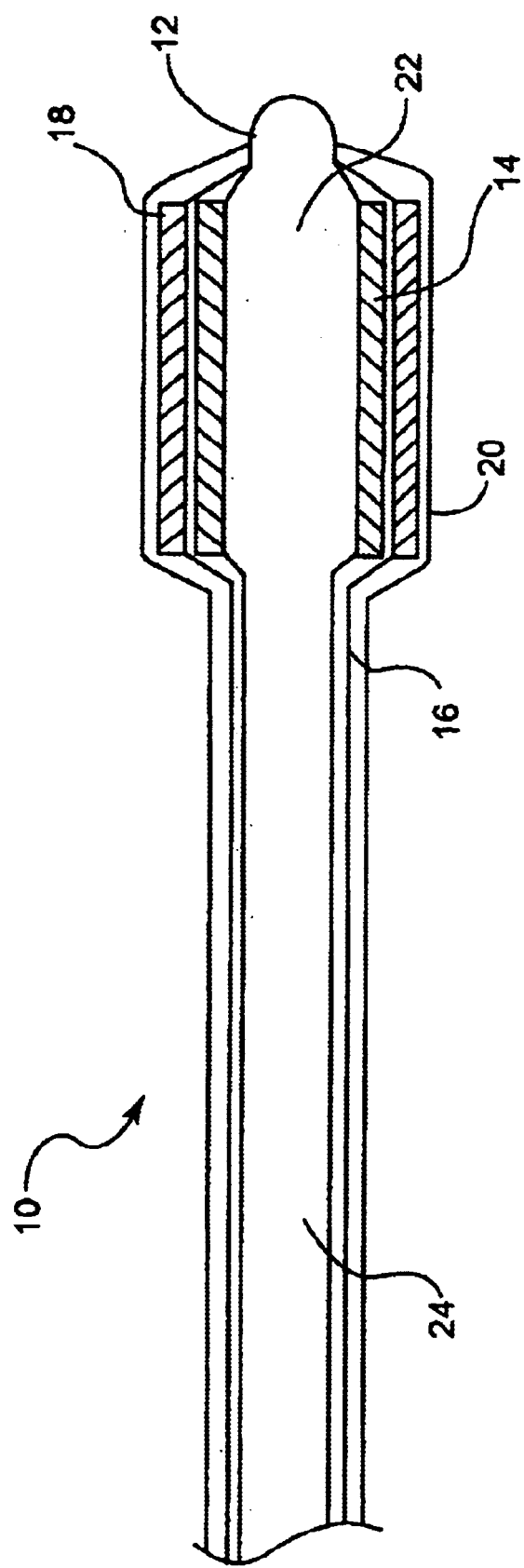
FIG. 2 is a side elevational view of another embodiment of the invention.

In the embodiment shown in FIG. 1 stents 14 and 18 may be self-expanding stents constructed from a shape memory metal such as nitinol or other material such as a shape memory polymer material. However, in certain instances it may be desirable to employ a balloon expandable stent or prosthesis. Where a balloon expandable stent is included for delivery by catheter 10, a portion of the distal end 12 of the catheter 10 may be equipped with a medical balloon 22 such as is shown in FIG. 2.

Where catheter 10 includes a balloon 22, the catheter includes a proximally extending inflation lumen 24 which is in fluid communication with the balloon 22 in order to provide inflation fluid to the balloon interior as is know in the art. Where one or more of stents 14 and 18 are self-expandable, balloon 22 may be used to further mechanically expand or seat the stents into place once they are fully self-expanded. Alternatively, in the embodiment shown in FIG. 2, inner stent 14 may be a balloon expandable stent which may be expanded to its delivery diameter through inflation of balloon 22. Expansion of such a balloon expandable stent will typically occur after delivery of any outer stents, such as stent 18, and retraction of sheathes, such as sheathes 16 and 20. Once inner stent 14 has been expanded by balloon 22, the balloon may be used to further expand or seat self-expanding stent 18.

Figure 3:
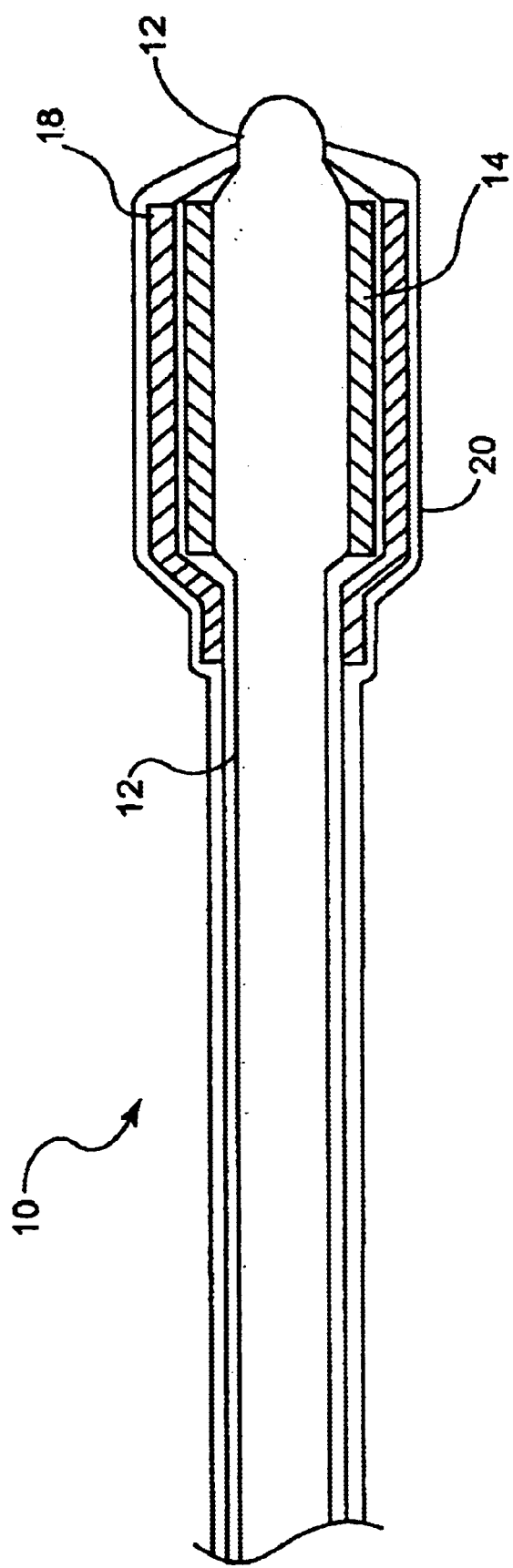
FIG. 3 is a side elevational view of another embodiment of the invention.

As indicated above, it is not necessary that stents 14 and 18 a have the same structural properties or characteristics. Not only may the stents 14 and 18 have different expansion characteristics, the stents may also be configured to have different shapes, sizes, strut patterns etc. For example, as shown in FIG. 3, one of the stents, such as for example stent 18, may have a greater length than the other stent 14. Stents of differing lengths may be useful for treating multiple legions of unequal lengths in a vessel or vessel branches.

In the embodiment shown in FIG. 3, outer stent 18 is shown as being longer than inner stent 14. It should be noted however, that any stent used with catheter 10 may be provided with a desired length independent of the length of the remaining stents. Relative radial position on the catheter of a stent of a given length may likewise be varied. That is to say: where it is desired to provide one or more stents with a length greater than other stents, the longer stents may be radially inward or outward of the shorter stents as desired.

Figure 4:
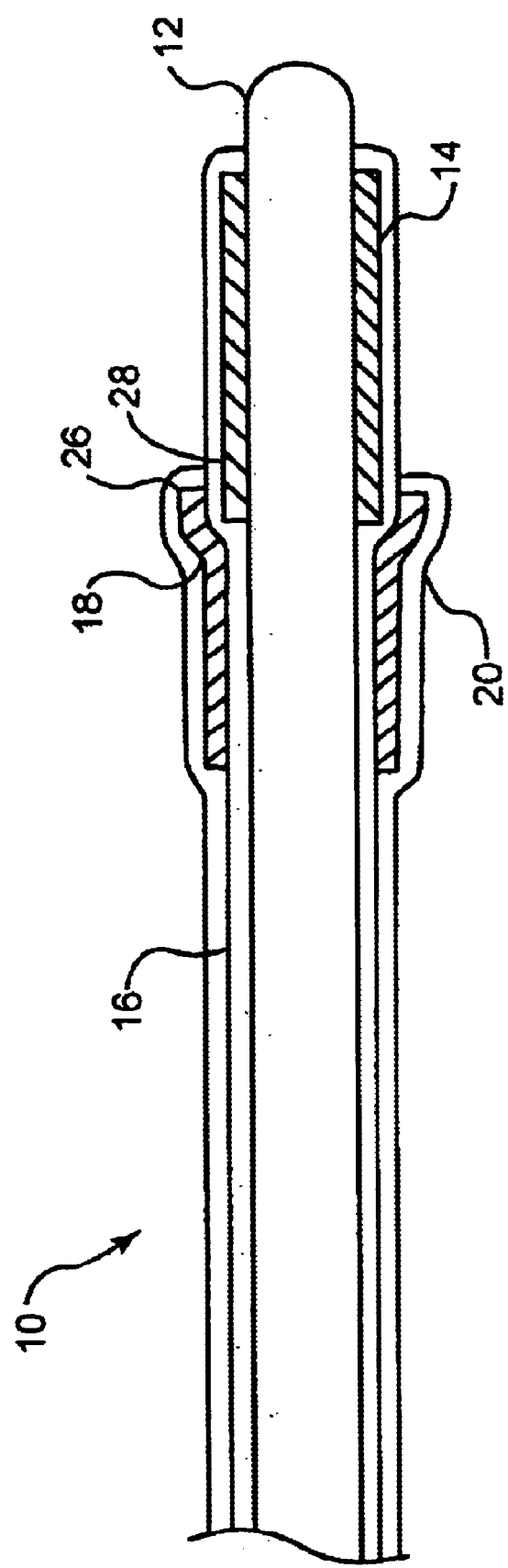
FIG. 4 is a side elevational view of another embodiment of the invention.

The position of the stents 14 and 18 may also be varied longitudinally as well. For example, in the embodiment shown in FIG. 4, the distal end 26 of stent 18 is shown overlapping only a proximal portion 28 of the inner stent 14. The stents of the present invention may overlap to any degree and in any configuration, however, partial overlap of the stents may provides a reduction of the length of the least flexible cross-section as well as the largest diameter of the combined stents 14 and 18.

It has been discussed that the relative size, shape, structure, position other features of the stents may be varied as desired. A further aspect of the invention which may be varied is the number of stents which may be associated with the catheter 10. For example, in the embodiments shown in FIGS. 1–4 the catheter assembly 10 is shown having only two stents 14 and 18 positioned thereon. However, in the alternative embodiment shown in FIG. 5, the catheter is shown equipped with three partially overlapping stents 14, 18, and 28. Stent 28 also include a retaining sheath 30 which has the same characteristics and function as sheathes 16 and 20 previously described.

Figure 5:
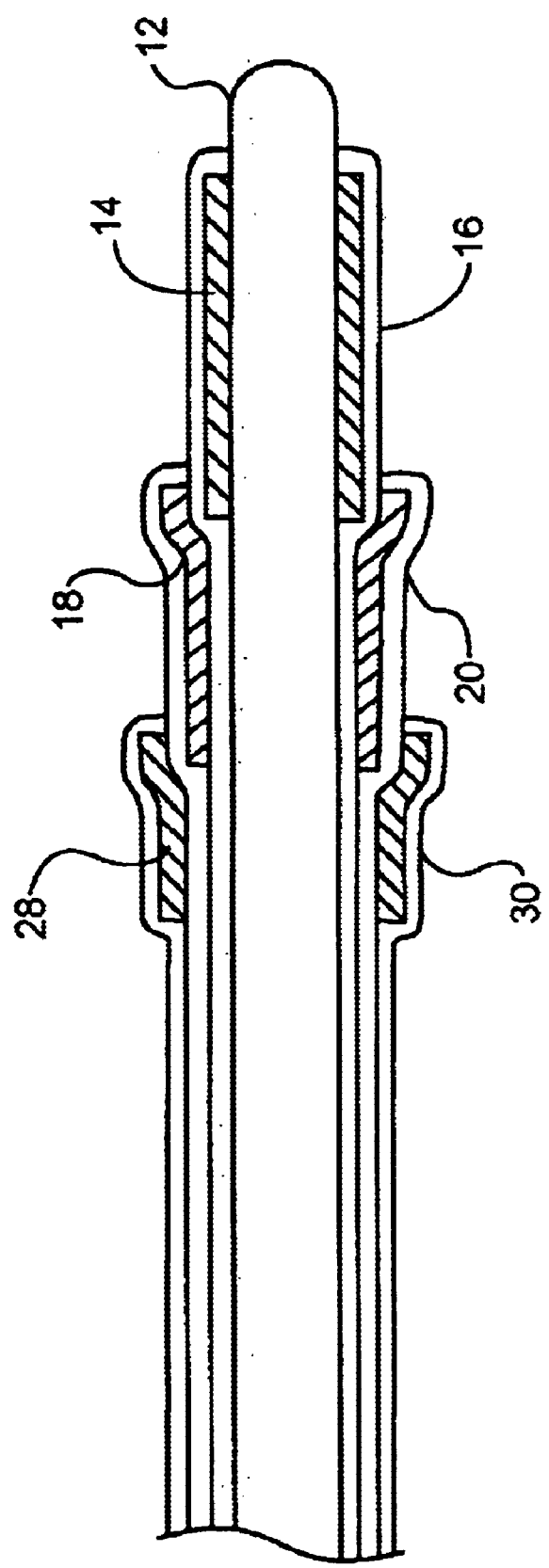
FIG. 5 is a side elevational view of another embodiment of the invention.

Regardless of the number of stents to be delivered by catheter 10, the stents may have a variety of characteristics such as size, shape, construction, expansion characteristics, etc. such as has been previously described in relation to FIGS. 1–4. One of ordinary skill in the art will recognize that the particular overlapping configuration of stents 14, 18, and 28 shown in FIG. 5 is merely one example of a wide variety of configurations of the catheter assembly 10 and that other configurations of stents of the same or different size, shape, construction, and expansion types may be employed with the present invention.

Figure 6:
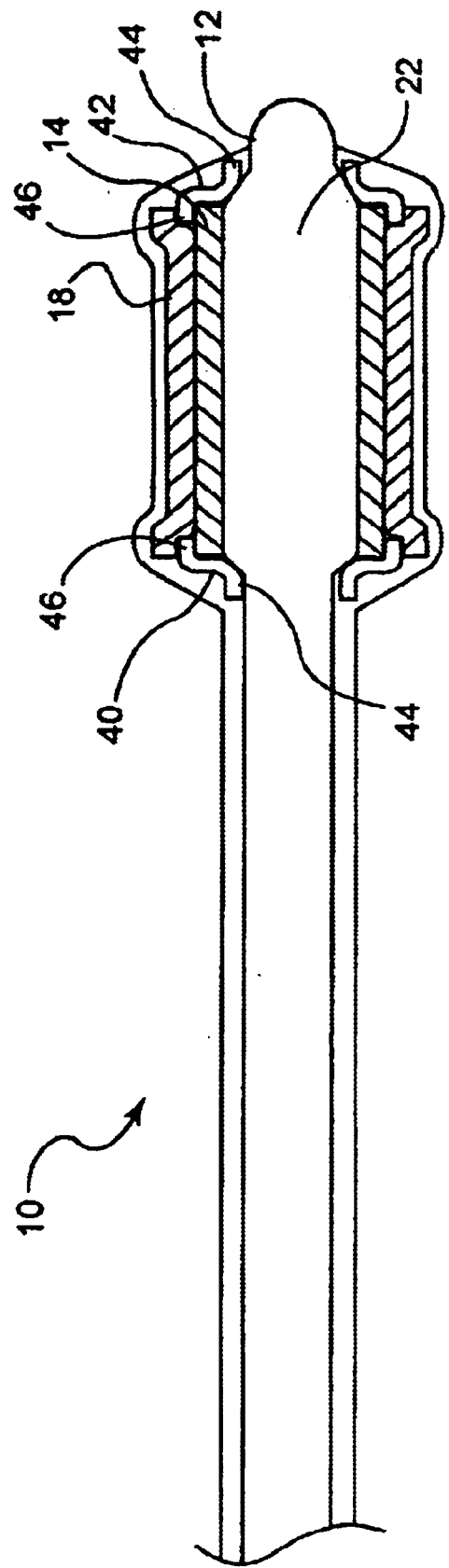
FIG. 6 is a side elevational view of yet another embodiment of the invention.

While the above description has paid particular attention to the wide variety of multiple stent configurations which may be utilized with catheter 10, it must also be noted that a variety of sheathes or sleeves may also be utilized to cover or retain the stents in the reduced state prior to delivery. In FIGS. 1–4 proximally retractable sheathes 16 and 20 are shown (in FIG. 5, proximally retractable sheath 30 is also shown). However, alternative forms of sheathes, such as self-retracting sleeves 40 and 42, examples of which are shown in FIG. 6. Self-retracting sleeves 40 and 42 are particularly useful in retaining a balloon expandable stent, such as stent 14, in place about the balloon 22 prior to delivery of the stent 14. An example of sleeves 40 and 42 is described in U.S. Pat. No. 4,950,227 to Savin et al., which relates to a balloon expandable stent delivery system in which a sleeve overlaps the distal or proximal margin (or both) of a stent during delivery. During inflation of the stent at the deployment site, the stent margins are freed of the protective sleeve(s) and the sleeve(s) then collapse upon the delivery catheter for removal.

As may be seen sleeves 40 and 42 have ends 44 which are engaged to portions of the catheter adjacent to the balloon 22. The sleeves 40 and 42 extend from ends 44 over at least a portion of stent 14 end terminate in end 46. The sleeves 40 and 42 may extend over the entire length of the stent 14 and may even abut or engage one another prior to stent delivery. Examples of sleeves which engage one another are described in U.S. app. Ser. No. 09/552807 filed Apr. 20, 2000 and entitled Fully Sheathed Balloon Expandable Stent Delivery System, the entire contents of which is incorporated herein by reference.

As indicated above, in order to expand a balloon expandable stent, such as stent 14, outer sheath(es), such as sheath 20 must first be retracted to allow self-expanding stents, such as stent 18 to expand outward from the catheter. Once the outer sheath(es) and stent(s) are deployed, balloon 22 may be inflated to cause sleeves 40 and 42 to retract and allow stent 14 to be expanded and delivered. The sleeves 40 and 42 may be configured to remain on the ends of the balloon to aid in balloon collapse and removal of the catheter 10 from the body. Alternatively, the sleeves may retract fully off of the balloon 22 or may be biodegradable. Where the sleeves 40 and 42 are biodegradable the stent 14 may be a self-expanding stent with no need for balloon expansion.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

What is claimed is:

1. A stent delivery catheter comprising an inner member, the inner member having a first stent disposed thereabout and a second stent disposed about the first stent, the catheter further comprising a first retractable sheath between the first stent and the second stent and a second retractable sheath disposed about the second stent.

2. The stent delivery catheter of claim 1 further comprising a third stent disposed about the second sheath and a third retractable sheath disposed about the third stent.

3. The stent delivery catheter of claim 1 wherein each sheath is at least partially constructed from at least one material from the group consisting of thermoplastic elastomer, silicone, polyethylene, high density polyethylene, polytetrafluoroethylene, and any combinations thereof.

4. The stent delivery catheter of claim 1 wherein each sheath is at least partially constructed from at least one material from the group consisting of polyimide, polyamide, silicone and any combinations thereof.

5. The stent delivery catheter of claim 1 wherein the first stent has a length different than the second stent.

6. The stent delivery catheter of claim 1 wherein one of the stents is self-expanding and the other stent is balloon expandable.

7. The stent delivery catheter of claim 6 wherein the second stent is self-expanding.

8. The stent delivery catheter of claim 7 further comprising a medical balloon disposed within the first stent, the medical balloon in fluid communication with an inflation lumen.

9. The stent delivery balloon of claim 8 wherein the first sheath comprises a pair of stent retaining sleeves, each of the stent retaining sleeves having a first end and a second end, the first end of each stent retaining sleeve overlying a different end of the first stent, the second end of each stent retaining sleeve engaged to at least a portion of the catheter adjacent to the medical balloon, each of the stent retaining sleeves constructed and arranged to release the first stent when the medical balloon is inflated to a predetermined extent.

10. A method of treating a body comprising the steps of:
   a) providing a catheter comprising a plurality of stents including a first stent and a second stent, the first stent extending within the second stent,
   b) inserting the catheter in a bodily vessel and delivering the stents to a first desired location within the body;
   c) deploying one of the first and second stents at the first desired location;
   d) delivering the other of the first and second stents to a second desired location within the body, the second desired location different than the first desired location;
   e) deploying the other of the first and second stents at the second desired location.

11. The method of claim 10 wherein the second stent is self-expandable.

12. The method of claim 10, the catheter comprising a third stent disposed about the first and second stents, further comprising the steps of:
   f) delivering the third stent to a third desired location with the body;
   g) deploying the third stent at the third desired location within the body.

13. The method of claim 12 wherein the first stent self-expands during step d).

14. The method of claim 13 wherein the second stent is deployed by balloon expansion during step e).

15. The method of claim 12 wherein the first, second and third stents are deployed in the vicinity of a bifurcation in a bodily vessel.

16. The method of claim 10 the catheter comprising a first sheath between the first and second stents and a second sheath disposed about the second stent, wherein step c) includes withdrawing the second sheath from over the second stent.

* * * * *